(12) United States Patent
Watson

(10) Patent No.: US 7,129,389 B1
(45) Date of Patent: Oct. 31, 2006

(54) PUNCTURE SITE PATCH

(76) Inventor: Robert Watson, 1704 Singletree, Bowling Green, KY (US) 42103

( * ) Notice: Subject to any disclaimer, the term of this patent is extended or adjusted under 35 U.S.C. 154(b) by 26 days.

(21) Appl. No.: 10/252,625

(22) Filed: Oct. 29, 2002

(51) Int. Cl.
A61F 13/00 (2006.01)

(52) U.S. Cl. .......................... 602/48; 602/46; 128/888; 604/180

(58) Field of Classification Search ............ 602/41–59; 128/888, 889, 851, 859; 604/174–180, 192, 604/112, 116, 117
See application file for complete search history.

(56) References Cited

U.S. PATENT DOCUMENTS

| 4,607,633 | A | * | 8/1986 | Lauritzen ..................... 156/250 |
| 4,641,643 | A | * | 2/1987 | Greer .......................... 128/888 |
| 5,496,264 | A | * | 3/1996 | Watson et al. ................ 602/48 |
| 5,728,071 | A | * | 3/1998 | Watson et al. ............... 604/180 |
| 5,738,641 | A | * | 4/1998 | Watson et al. ................ 602/43 |

FOREIGN PATENT DOCUMENTS

GB    2224445 A  *  5/1990

* cited by examiner

Primary Examiner—Kim M. Lewis
(74) Attorney, Agent, or Firm—Jenkins, Wilson, Taylor, & Hunt, P.A.

(57) ABSTRACT

An elastomeric puncture site patch for adhering to skin and antiseptically covering the skin at an area where a sharp object such as a syringe needle or intravenous is to be inserted. The patch is comprised of an elastomeric transparent self-sealing membrane and a spacer having an aperture. The spacer has an adhesive film on the surface opposite the membrane for adhering the patch to the skin. When the patch is applied to an area of the skin, a chamber is formed between the skin and the membrane and bounded by the spacer. In use, the skin is antiseptically cleaned and the patch applied. The syringe needle or similar device punctures the membrane and the skin. At the end of the procedure the needle is withdrawn and any blood remaining on the outside of the needle or oozing from the wound is trapped in the chamber, thus preventing contamination of the area beyond the chamber. A method of manufacturing the puncture site patch is also provided.

44 Claims, 2 Drawing Sheets

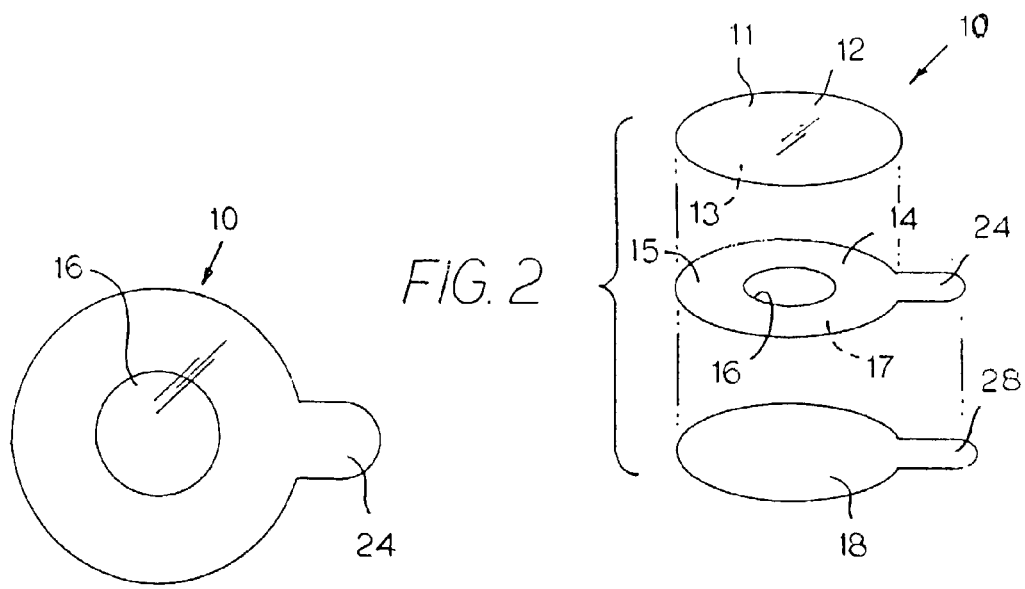
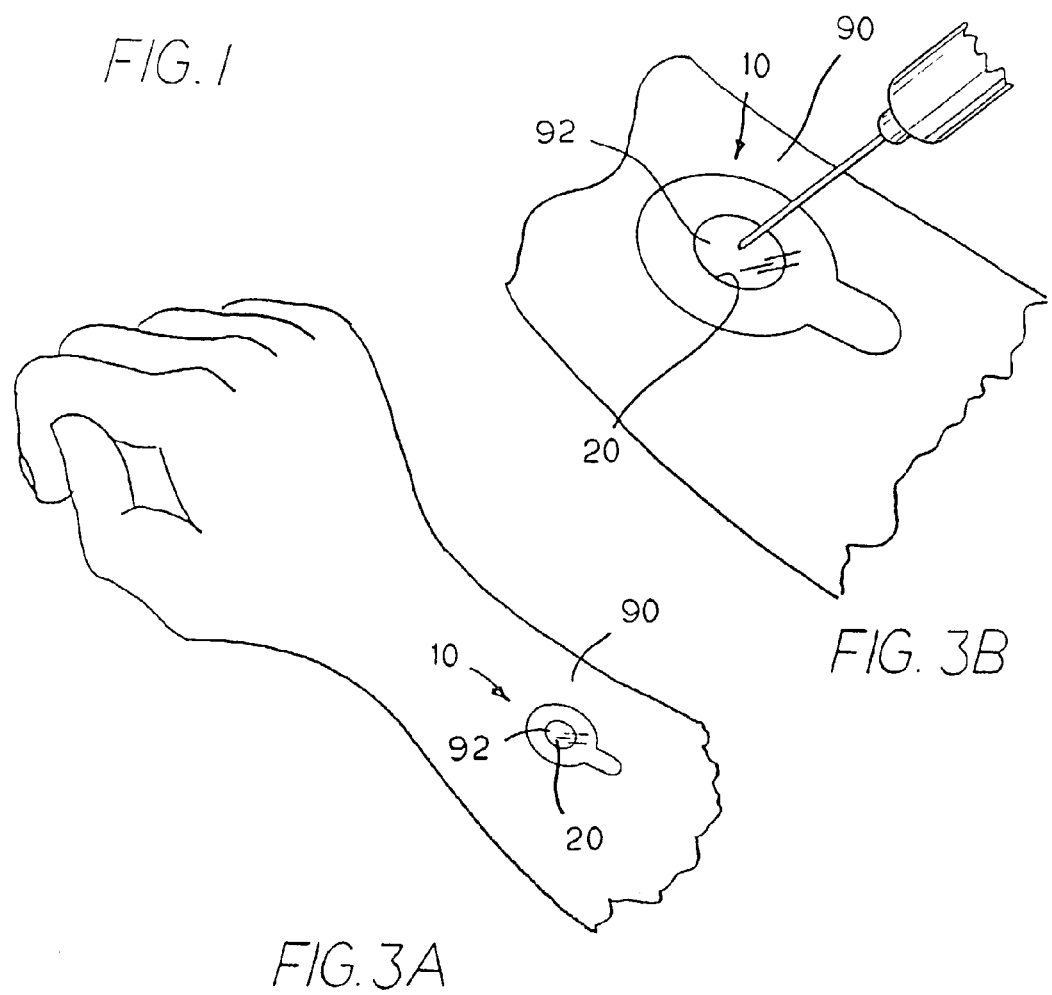

PUNCTURE SITE PATCH

BACKGROUND

This invention relates to an adhesive patch for use on humans or animals which is adhered to a patient's skin allowing a health care practitioner to puncture the patient's skin while minimizing the risk of contact with the patient's blood.

It is widely recognized that blood-borne pathogens are an important and serious method of transmission of infectious diseases. Health care practitioners, in particular, are in danger from such exposure because of the need to perform functions that directly expose the practitioner to blood, such as puncturing a patient's skin with a needle to make an injection or to withdraw blood. Typically, when the skin is to be punctured, the target area of the skin is wiped with a disinfectant and the needle (which may be further attached to a syringe) is injected through the skin subcutaneously or intramuscularly. After the skin has been punctured, the needle is withdrawn and a pad of gauze or cotton is placed on the puncture wound to absorb any blood which may emanate therefrom. The practitioner may come into contact with the blood at several points during this procedure, such as when the needle first punctures the skin, when the needle is removed from the skin but before the pad is positioned over the puncture wound, or after the pad is applied over the puncture site because blood may ooze from or seep through the pad.

Attempts have been made to provide a protective patch that is applied to the skin prior to the skin being punctured. For example, U.S. Pat. Nos. 5,728,071 and 5,738,641, both issued to the present applicant and incorporated herein in their entirety by reference, describe patches that adhere to the patient's skin and minimize the risk of blood contact during injections and blood withdrawal procedures, respectively. The '071 patch is a three layer system comprising a generally annular absorbent pad having a first surface to be placed against the skin of a patient around an intended injection site, a second surface opposite said first surface and a central opening; an elastomeric, self-sealing membrane through which an injection needle can penetrate, said membrane lying against said second surface and closing said central opening, said membrane, in use, being spaced from the patient's skin and forming a cavity between said membrane and said skin surrounded by said absorbent pad; and a cover layer having a central opening substantially aligned with said central opening of said pad and exposing a central portion of said membrane to identify the injection site. The '641 patch is a three layer system comprising an absorbent pad having a first surface to be placed against the skin of a patient around an intended penetration site for injection or withdrawal and a central opening; a transparent, elastomeric, self-sealing membrane through which a needle can penetrate; and a transparent cover layer having an outer surface and an adhesive surface for holding said membrane in said central opening of said pad and for adhering said patch to skin of a patient, and having a central opening substantially aligned with the central opening of said pad to expose a central portion of the membrane allowing visual identification of a selected penetration site whereby a blood vessel can be located through the membrane and cover and a needle can be passed through said membrane and the patient's skin into a vessel for injection or blood withdrawal, and whereby, after injection or withdrawal, the needle is extracted, the membrane wipes the needle and forms a cavity with the pad and the patient's skin to contain blood from the penetration site until after hemostasis. While these patches have been effective for restricting the free flow of blood when the skin is punctured, they are difficult to manufacture because of the need to carefully align the openings in the various layers. Further, the top surface layer of these patches is susceptible to degradation when wiped with an antiseptic. Therefore, each patch must be individually wrapped and sterilized and then carefully maintained sterile by the clinician while using since wiping with alcohol to maintain sterility may degrade the pad. Finally, neither patch provides a means for the blood to coagulate so a nominal risk remains that a practitioner could be exposed to blood oozing from the absorbent pad upon removing the patch from the patient.

Thus, it would be beneficial to have a protective patch for use during injections and blood withdrawal procedures that does not require complex registering of the layers, that is relatively easy and inexpensive to manufacture, that has a top surface that can be wiped with an antiseptic such as alcohol while using, and that may include a means for coagulating blood collected within the patch, thereby essentially eliminating the risk of unintended blood contact.

SUMMARY OF THE INVENTION

The present invention is for a puncture site patch for use on humans or on animals for confining blood from a needle wound and for a method of making the patch. The patch comprises an essentially transparent membrane layer and a spacer having an aperture. The membrane layer preferably is a transparent, self-sealing, non-coring elastomeric material through which an injection needle can penetrate and which is self-sealing when the needle is removed to prevent blood from flowing out through the puncture hole made by the needle in the membrane. The membrane layer will not degrade if wiped with an antiseptic such as alcohol. This allows the clinician the option of wiping the surface of the patch immediately before injection in case the sterile field is breached and alleviates the need to individually wrap and sterilize each patch. The spacer is a material sheet that is adhered to the membrane and that has an adhesive film on the opposite side to adhere the patch to a patient's skin. When the patch is secured on the patient's skin, a cavity is formed between the skin and the membrane, bounded by the spacer.

In an alternative embodiment of the patch, a coagulating agent is positioned along the inner edge of the spacer and is included at sufficient concentration that any blood which escapes into the cavity can be coagulated, or gelled, thereby preventing free flow of blood when the patch is removed from the patient's skin.

BRIEF DESCRIPTION OF THE DRAWINGS

FIG. 1 is a top view of the puncture site patch of the present invention;

FIG. 2 is an exploded perspective view of the patch of FIG. 1;

FIGS. 3 and 3A are perspective views of the patch of FIG. 1 positioned on a patient's arm.

DESCRIPTION OF THE PREFERRED EMBODIMENTS

Figure 4:
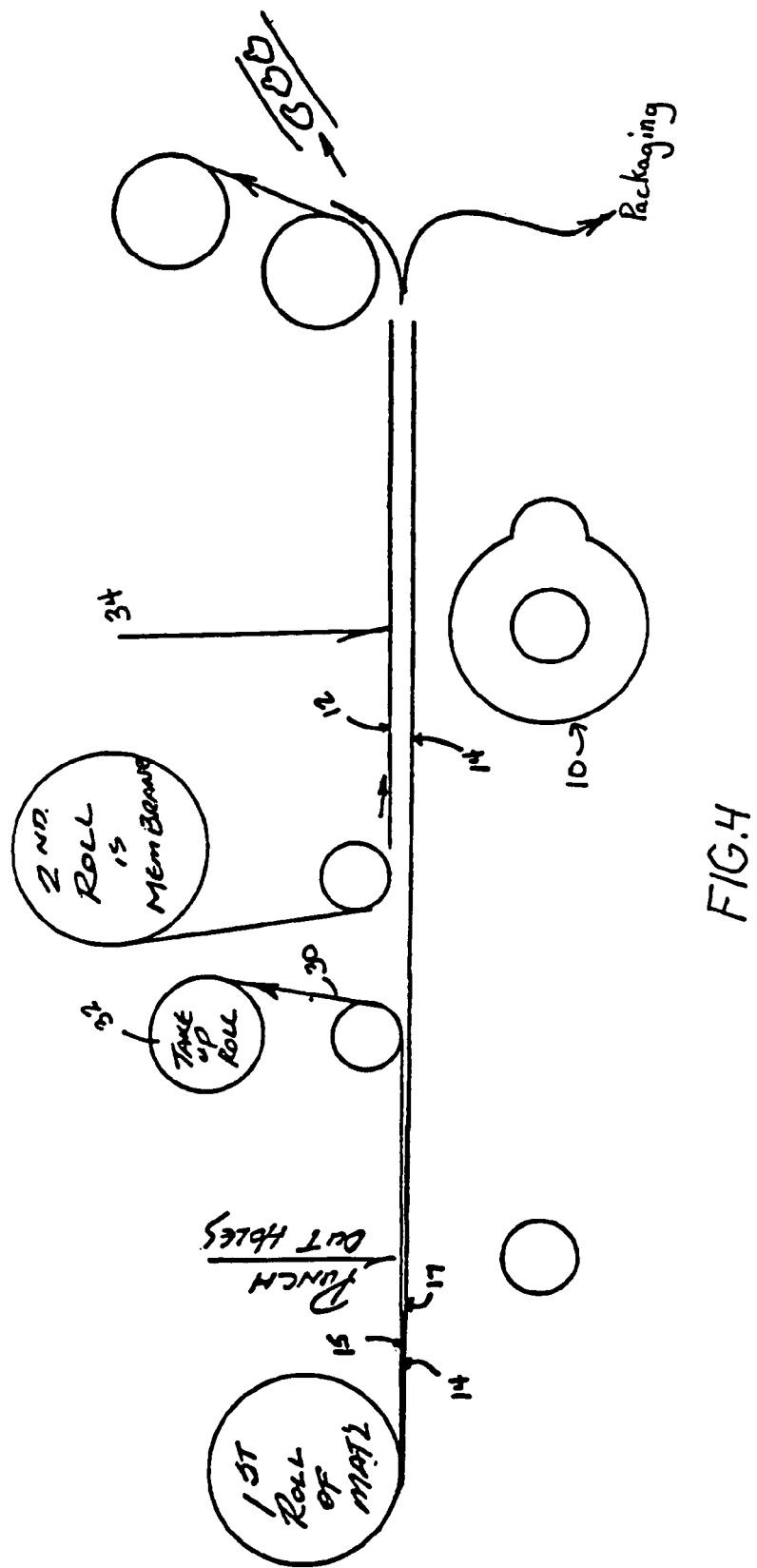
FIG. 4 is a schematic view of a process by which the patch of FIG. 1 can be made.

Before discussing the structure of the invention in detail, it will be noted that the layers of material used in the structure are quite thin. In the various figures, the thicknesses are exaggerated for clarity of illustration and it will be realized that this exaggeration also exaggerates the curvatures that occur in the drawings at the overlapping intersections of various layers.

FIGS. 1 and 2 show a puncture site patch indicated generally by the numeral 10 made in accordance with the invention. The patch 10 includes a membrane 12 and a spacer 14, having an aperture 16. In the embodiment shown, the patch 10 is essentially circular, but other shapes can be used without departing from the scope of the present invention. As shown in FIGS. 3A and 3B, the patch 10 is applied to a patient's skin 90 over an intended injection site 92. When the patch 10 is attached to the skin 90, a cavity 20 forms between the skin 90 and the membrane 12 bounded by the spacer 14.

Referring to FIGS. 1 and 2, the membrane 12 of the patch 10 is an elastomeric material, preferably sterile, self-sealing, non-coring, non-latex and FDA-approved for direct contact with human or animal skin. More preferably, the membrane 12 is sufficiently transparent that the practitioner can observe the patient's skin 90 when the patch 10 is positioned over the intended injection site 92. Further, the membrane material is preferably selected such that it is essentially unaffected chemically or structurally, and therefore will not degrade if cleaned, disinfected and/or sterilized with agents such as ethyl alcohol, betadine, or similar common disinfectants. The membrane 12 has and exterior face 11 and an interior face 13, which faces toward the patient's skin 90 when the patch 10 is applied. The membrane 12 can have any convenient shape, but must have dimensions sufficient to cover the spacer 14. In a preferred embodiment, the exterior peripheries of the membrane 12 and spacer 14 are essentially identical.

The spacer 14 is a thin material sheet having an outer face 15 and an inner face 17. The spacer 14 can be composed of any material that can be sterilized and that can be used in direct contract with human skin, such as nylon, polyurethane, polyethylene, polypropylene, isoprene, cotton, linen, or combinations thereof. Optionally, the material for the spacer 14 may be selected on the basis of its ability to absorb blood and bodily fluids, although these absorptive properties are not required. However, if an absorbent material is used, it is preferable, but not required, that the material be somewhat resistant to wicking to minimize the risk of blood wicking from the cavity 20 to the outside edge 19 of the spacer 14. The spacer 14 is secured by its outer face 15 to the interior face 13 of the membrane 12. A variety of means known in the art can be used to secure the spacer 14 to the membrane 12, such as glue, hot melt adhesive, pressure sensitive adhesive, thermally sensitive adhesive, chemical bonding, acrylic cement, or a combination thereof, or any other means well known in the art. Preferably, the spacer 14 is positioned on the membrane 12 such that the membrane 12 covers the entire outer face 15 of the spacer 14. The inner face 17 of the spacer 14 is coated with an adhesive film (not shown) for holding the patch 10 against the patient's skin 90. Although a variety of adhesives may perform the desired function, it is preferable that the adhesive be an FDA-approved material because of the direct skin contact. Optionally, a protective sheet or release paper 18 can be used to protect the adhesive coating until the patch 10 is applied to the skin 90, with the release paper 18 being any of a variety of materials known in the art. The release paper 18 may have a similar size and shape as the spacer 14, or it may be slightly larger than the spacer 14 thereby creating tab 28 to allow for easy removal of the release paper 18 from the membrane 12 and spacer 14.

The spacer 14 further includes the aperture 16 near its center. The aperture 16 must have dimensions adequate to allow the practitioner to insert a needle through the membrane 12 and the aperture 16 without penetrating any part of the spacer 14. When the patch 10 is applied to the skin 90, the aperture 16 bounded by the skin 90, the membrane 12, and the spacer 14 forms the cavity 20. Because the needle passes through the cavity 20 during an injection or blood withdrawal procedure, any blood that is released from the skin will pool in the cavity 20. The blood may dry within the cavity 20 over time, or it may be absorbed by the spacer 14 if the spacer 14 includes an absorbent material, or optionally, a coagulating agent may be applied to the spacer 14 adjacent to the aperture 16 to cause the blood to thicken and gel. In a preferred embodiment, the spacer 14 is made from polyethylene, and the aperture edge of the spacer 14 is coated with oxidized regenerated cellulose or any other suitable coagulant as is generally known in the art to coagulate any blood that enters the cavity 20. In a more preferred embodiment, the dimensions of the aperture are such that the cavity 20 formed can contain up to about 0.3 cc of bodily fluids.

Ideally, the patch 10 is secured and held directly against the patient's skin 90 along any portion of the inner face 17 of the spacer 14. While the secure attachment is beneficial to prevent blood leakage, it can be problematic for removing the patch from the skin after use. To make removal easier, the patch may further include pull tab 24 that protrude from the spacer 14. The pull tab 24 is preferably unitary with the spacer 14. The pull tab 24 may or may not include adhesive on the inner face 17. Thus, the practitioner can easily grab the loose pull tab 24 to remove the patch from the patient's skin.

A patch made in accordance with the invention can also be used when inserting a catheter into a patient, when inserting a needle for biopsies, or whenever the patient's skin will be punctured by a sharp, needle-like object. The cavity can accommodate bodily fluids other than blood, and a variety of antimicrobial agents may be substituted on the spacer for the coagulating agent if so desired.

The patch of the present invention is relatively easy and inexpensive to manufacture. For example, as shown in FIG. 4, the patch 10 may be made using a continuous production process that includes creating apertures 16 at predetermined positions on a sheet of spacer material 14 that is pretreated with adhesive on both faces 15, 17 and that includes one sheet of protective paper 30 on the outer face 15 and the sheet of release paper 18 on the inner face 17, then removing the protective paper 30 using a take-up roll 32 as the punched spacer material continues its forward motion, then securing a sheet of membrane material 12 to the outer face 15, then die cutting 34 the membrane/spacer/release paper in the desired configuration. As is known in the art, the process may be modified in a variety of ways without departing from the scope of the invention, such as applying the first adhesive to the membrane rather than the spacer sheet, applying the second adhesive to the release paper rather than the spacer sheet, using lasers to cut the layered material, layering and cutting the membrane and spacer before adding the release sheet and combinations thereof.

While certain advantageous embodiments have been chosen to illustrate the invention, it will be understood by those skilled in the art that various modifications can be made herein without departing from the scope of the invention.

What is claimed is:

1. A puncture site patch for adhering to skin, comprising:
   an elastomeric, self-sealing membrane through which an injection needle can penetrate, the membrane having an exterior face and an interior face;
   a spacer having an outer face and an inner face, the spacer defining an aperture and being attached at said outer face to said interior face of said membrane, wherein said spacer comprises an absorptive material resistant to wicking; and
   an adhesive film for adhering to skin, said adhesive film coating said inner face of said spacer.

2. The puncture site patch of claim 1, wherein said membrane is transparent and has a surface area large enough to completely cover said aperture.

3. The puncture site patch of claim 2, wherein said membrane is a non-coring membrane.

4. The puncture site patch of claim 1, wherein said spacer is a material that can be sterilized without degrading.

5. The puncture site patch of claim 4, wherein said spacer comprises a material selected from the group consisting of nylon, polyurethane, polyethylene, polypropylene, isoprene, cotton, linen and combinations thereof.

6. The puncture site patch of claim 5, further comprising a pull tab extending from a periphery of said spacer.

7. The puncture site patch of claim 6, wherein said adhesive film coats only said spacer.

8. The puncture site patch of claim 4, wherein said spacer is polyurethane.

9. The puncture site patch of claim 4, further comprising a coagulating agent coating an edge of said spacer, said edge located adjacent said aperture.

10. The puncture site patch of claim 9, wherein said coagulating agent is oxidized regenerated cellulose.

11. The puncture site patch of claim 1 further comprising a release paper in direct contact and completely covering said adhesive film.

12. The puncture site patch of claim 11, wherein said release paper has a surface area slightly larger than a total surface area of said adhesive film so as to create a removal tab for said release paper.

13. A sterile puncture site patch for adhering to skin, consisting essentially of:
   an essentially transparent, self-sealing, non-coring, elastomeric membrane having an exterior face and an interior face;
   a spacer having an outer face and an inner face bonded at said outer face to said interior face of said membrane;
   an adhesive film for adhering to skin, said adhesive film coating said inner face of said spacer; and
   an aperture through said spacer, said aperture positioned in relation to said spacer and said membrane so that when said sterile puncture site patch is adhered to said skin a cavity is formed between said skin and said membrane and bounded by said spacer.

14. The sterile puncture site patch of claim 13, wherein said self-sealing membrane comprises a thermoplastic, non-coring, self-sealing, non-degrading by sterilization material.

15. The sterile puncture site patch of claim 13, wherein said spacer comprises a material selected from the group consisting of nylon, polyethylene, polypropylene, isoprene, cotton, linen and combinations thereof.

16. The sterile puncture site patch of claim 15, wherein said spacer is polyethylene.

17. The sterile puncture site patch of claim 13, wherein said spacer comprises an absorptive material.

18. The sterile puncture site patch of claim 17, wherein said absorptive material is resistant to wicking.

19. The sterile puncture site patch of claim 13, further comprising a coagulating agent coating an edge of said spacer, said edge located adjacent said aperture.

20. The sterile puncture site patch of claim 19, wherein said coagulating agent is oxidized regenerated cellulose.

21. A continuous production process method for manufacturing a puncture site patch, comprising:
   a) punching apertures at predetermined positions through a sheet of a spacer material comprising an absorptive material resistant to wicking having an inner face adhesive surface and an outer face adhesive surface, said outer face adhesive surface covered with a release liner;
   b) removing said protective paper from said outer face adhesive surface of said spacer material with a take up roll;
   c) securing a sheet of an elastomeric, self-sealing membrane material through which an injection needle can penetrate to said outer face adhesive surface; and
   d) die cutting said spacer material, said release liner and said secured membrane in a preferred configuration to produce a puncture site patch.

22. The continuous production process method of claim 21, further comprising:
   e) packaging said puncture site patch into an interior of a package; and
   f) sterilizing said puncture site patch and said interior of said package.

23. A puncture site patch for adhering to skin, comprising:
   a spacer defining an aperture and having an outer face and an inner face, the outer face adapted for being secured to a membrane and the inner face adapted for adhering to skin;
   a pull tab extending from a periphery of said spacer;
   the membrane comprising an elastomeric, self-sealing membrane, and the membrane having an exterior face and an interior face, the membrane interior face adapted for being secured to the outer face of the spacer; and
   whereby an injection needle can penetrate through the membrane, through the aperture and into skin.

24. A puncture site patch for adhering to skin, comprising:
   an elastomeric, self-sealing membrane through which an injection needle can penetrate the membrane having an exterior face and an interior face, and wherein the exterior face is completely exposed;
   a spacer having an outer face and an inner face secured at said outer face to said interior face of said membrane;
   an adhesive film for adhering to skin, said adhesive film coating said inner face of said spacer; and
   an aperture through said spacer.

25. The puncture site patch of claim 24, wherein said membrane is transparent and has a surface area large enough to completely cover said aperture.

26. The puncture site patch of claim 25, wherein said membrane is a non-coring membrane.

27. The puncture site patch of claim 24, wherein said spacer is a material that can be sterilized without degrading.

28. The puncture site patch of claim 27, wherein said spacer comprises a material selected from the group consisting of nylon, polyurethane, polyethylene, polypropylene, isoprene, cotton, linen and combinations thereof.

29. The puncture site patch of claim 28, further comprising a pull tab extending from a periphery of said spacer.

30. The puncture site patch of claim 28, wherein said adhesive film coats only said spacer.

31. The puncture site patch of claim 27, wherein said spacer is polyurethane.

32. The puncture site patch of claim 27, wherein said spacer comprises an absorptive material.

33. The puncture site patch of claim 32, wherein said absorptive material is resistant to wicking.

34. The puncture site patch of claim 27, further comprising a coagulating agent coating an edge of said spacer, said edge located adjacent said aperture.

35. The puncture site patch of claim 34, wherein said coagulating agent is oxidized regenerated cellulose.

36. The puncture site patch of claim 24, further comprising a release paper in direct contact and completely covering said adhesive film.

37. The puncture site patch of claim 36, wherein said release paper has a surface area slightly larger than a total surface area of said adhesive film so as to create a removal tab for said release paper.

38. A method for providing an injection, comprising:
adhering a spacer to skin, the spacer defining an aperture, and the spacer having an outer face and an inner face and comprising an absorptive material resistant to wicking, the inner face being secured to the skin and the outer face having an elastomeric, self-sealing membrane secured to the outer face, the membrane comprising an exterior face that is at least substantially exposed; and injecting a needle through the membrane, through the aperture of the spacer, and into the skin.

39. A puncture site patch for adhering to skin, comprising:
an elastomeric, self-sealing membrane through which an injection needle can penetrate, the membrane having an exterior face and an interior face;
a spacer having an outer face and an inner face, the spacer defining an aperture and being attached at said outer face to said interior face of said membrane, wherein said spacer comprises a material that can be sterilized without degrading, which is selected from the group consisting of nylon, polyurethane, polyethylene, polypropylene, isoprene, cotton, linen and combinations thereof;
an adhesive film for adhering to skin, said adhesive film coating said inner face of said spacer; and
a pull tab extending from a periphery of said spacer.

40. The puncture site patch of claim 39, wherein said adhesive film coats only said spacer.

41. A sterile puncture site patch for adhering to skin, consisting essentially of:
an essentially transparent, self-sealing, non-coring, elastomeric membrane having an exterior face and an interior face;
a spacer having an outer face and an inner face bonded at said outer face to said interior face of said membrane, wherein said spacer comprises an absorptive material resistant to wicking;
an adhesive film for adhering to skin, said adhesive film coating said inner face of said spacer; and
an aperture through said spacer, said aperture positioned in relation to said spacer and said membrane so that when said sterile puncture site patch is adhered to said skin a cavity is formed between said skin and said membrane and bounded by said spacer.

42. A puncture site patch for adhering to skin, comprising:
an elastomeric, self-sealing membrane through which an injection needle can penetrate the membrane having an exterior face and an interior face, and wherein the exterior face is at least substantially exposed;
a spacer having an outer face and an inner face secured at said outer face to said interior face of said membrane, wherein said spacer comprises a material that can be sterilized without degrading, which is selected from the group consisting of nylon, polyurethane, polyethylene, polypropylene, isoprene, cotton, linen and combinations thereof;
an adhesive film for adhering to skin, said adhesive film coating said inner face of said spacer;
an aperture through said spacer; and
a pull tab extending from a periphery of said spacer.

43. The puncture site patch of claim 42, wherein said adhesive film coats only said spacer.

44. A puncture site patch for adhering to skin, comprising:
an elastomeric, self-sealing membrane through which an injection needle can penetrate the membrane having an exterior face and an interior face, and wherein the exterior face is at least substantially exposed;
a spacer having an outer face and an inner face secured at said outer face to said interior face of said membrane, wherein said spacer comprises an absorptive material resistant to wicking that can be sterilized without degrading;
an adhesive film for adhering to skin, said adhesive film coating said inner face of said spacer; and
an aperture through said spacer.

* * * * *